US00PP30402P3

(12) United States Plant Patent
Hanna et al.

(10) Patent No.: US PP30,402 P3
(45) Date of Patent: Apr. 16, 2019

(54) ***MISCANTHUS SINENSIS* PLANT NAMED 'M77'**

(50) Latin Name: *Miscanthus sinensis*
Varietal Denomination: M77

(71) Applicant: University of Georgia Research Foudation, Inc., Athens, GA (US)

(72) Inventors: Wayne W. Hanna, Chula, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 49 days.

(21) Appl. No.: 15/731,564

(22) Filed: Jun. 28, 2017

(65) Prior Publication Data

US 2019/0008081 P1 Jan. 3, 2019

(51) Int. Cl.
*A01H 5/12* (2018.01)
*A01H 6/46* (2018.01)

(52) U.S. Cl.
USPC ..... Plt./384
CPC ..... *A01H 6/46* (2018.05); *A01H 5/12* (2013.01)

(58) Field of Classification Search
USPC ..... Plt./384
CPC ..... A01H 5/12
See application file for complete search history.

*Primary Examiner* — Kent L Bell
(74) *Attorney, Agent, or Firm* — Klarquist Sparkman, LLP

(57) ABSTRACT

A new variety of *Miscanthus sinensis* plant named 'M77' produces a reduced number of seeds, making it less invasive.

2 Drawing Sheets

Latin name of the genus and species of the plant claimed: 'M77' is a vegetatively propagated ornamental perennial *Miscanthus* cultivar of the genus and species *Miscanthus sinensis*.

Variety denomination: The new *Miscanthus sinensis* claimed is of the cultivar denominated 'M77'.

BACKGROUND OF THE INVENTION

The present invention relates to a new and distinct cultivar of *Miscanthus sinensis* herein referred to as 'M77'.

The new *Miscanthus sinensis* is a product of a planned research, evaluation, and testing program conducted by the Inventors in Tifton, Ga. The objective of the *Miscanthus sinensis* research program is to create a new plant cultivar with reduced seed production. This cultivar is commercially important for its superior ornamental value and low seed production. These and other qualities are enumerated herein.

There is a need for a seed sterile *Miscanthus* cultivar because *Miscanthus* cultivars produce higher seed set at higher elevations which tend to make this genus invasive. Unprotected roots of respective groups of 59, 44, and 49 *Miscanthus sinensis* 'Gracillimus' plants were irradiated with 4-, 8-, and 12-Kr, respectively, of Cobalt 60 radiation and transplanted to a test field at Tifton, Ga. on Apr. 21, 2006. On Aug. 9, 2006, 37 and 1 plants were observed to have survived the 4-Kr treatment, and one plant was observed to have survived the 8-Kr treatment. Seven plants from the 4-Kr treated plants had tillers with reduced seed set. One plant, designated 4-22-1-1, had tillers with no seed set. A culm from 4-22-1-1 was designated M8-4 in 2008 and observed for seed set thru 2009 at Tifton, Ga. (elevation about 350 ft.). In 2010, M8-4 was designated as M8 and planted at Blairsville, Ga. (elevation about 1,880 ft.) in 2010. In 2010, M8 produced one seed per inflorescence at Tifton, Ga. and no seed at Blairsville, Ga. while the *Miscanthus sinensis* 'Gracillimus' control plants produced numerous seeds per inflorescence at both locations in non-replicated tests. The seed sterile plant observed at Blairsville, Ga. (high elevation) was designated 'M77'. This 'M77' plant was then asexually propagated by vegetative propagation. The resulting 'M77' plants were tested at Tifton, Ga. and Blairsville, Ga. in replicated tests from 2012 thru 2015. Tests consisted of five and three single plant replications arranged in a randomized complete block experiment at Tifton, Ga. and Blairsville, Ga., respectively.

Asexual reproduction of the new *Miscanthus* 'M77' by vegetative propagation (single stem propagules) in a controlled environment in Tifton, Ga. and Blairsville, Ga. since 2012, has shown that the unique features of this new *Miscanthus sinensis* cultivar are stable and reproduced true to type in successive generations.

SUMMARY OF THE INVENTION

The following traits have been repeatedly observed and represent the characteristics of a new *M. sinensis* cultivar 'M77'. The new cultivar 'M77' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed for the new *M. sinensis* cultivar 'M77' in Tifton, Ga. and Blairsville, Ga. and can be compared to *M. sinensis* 'Gracillimus':

1. 'M77' plants produce few seeds, especially at high elevations.
2. 'M77' plants exhibit a vigorous growth habit.
3. 'M77' plants are highly seed sterile.

The new cultivar *Miscanthus* 'M77' can be compared to its parent, *Miscanthus sinensis* var. *Gracillimus*.

Plants of the new *Miscanthus* 'M77' differ from its parent 'Gracillimus', at least in the following characteristic:

The new cultivar 'M77' produces significantly fewer seeds compared to 'Gracillimus', the closest known variety. In addition, the few seeds that 'M77' produces also have been observed to have significantly less germination potential than seeds of 'Gracillimus'. In one observation: (1) seeds from 'M77' plants growing at Tifton, Ga. did not germinate; while 'Gracillimus' seeds germinated at a 42% rate (LSD–5%=17); and (2) seeds from 'M77' plants growing at Blairsville, Ga. germinated at a 32% rate; while 'Gracillimus' seeds germinated at a 70% (LSD–5%=15). Inflorescences from numerous plants of 'M77' had to be searched in order to obtain enough 'M77' seeds for germination. Also, on average the height of 'M77' inflorescences are less than the height of 'Gracillimus' inflorescences.

The following observations, measurements, and values describe plants grown in Tifton, Ga. and Blairsville, Ga. In Tables 1-7, the least significant difference (LSD) is set at $P \leq 0.05$ probability level. Growth days were included in ratings. Plants were spaced 2 meters center to center spacing. Plants were established as single stem propagules in mid-April to mid-May and rated in September through October. Data was taken from plants during year of establishment in 2012 at Tifton, Ga. and 2013 in Blairsville, Ga. Data were also taken in 2013 and 2014 from over-wintered 2012 and 2013 plants at Tifton, Ga. and in 2013 and 2015 from over-wintered 2012 plants at Blairsville, Ga.

Inflorescence height of the new cultivar 'M77' was significantly shorter than those of 'Gracillimus' in four of seven tests (Table 1). Height of the leaf canopy of 'M77' was significantly shorter than that of 'Gracillimus' in three of seven tests (Table 2). Canopy diameter was significantly narrower for 'M77' compared to 'Gracillimus' in only two of seven tests (Table 3). This appeared to be related to the year of establishment. There appeared to be only small differences in canopy diameter between 'M77' and 'Gracillimus' after the year of establishment. As expected, plants tended to become more robust as they become older. Differences in inflorescence length appeared to be small between the 'M77' and 'Gracillimus' and significant only in two of three years at Tifton, Ga. (Table 4). 'M77' usually had fewer inflorescences than 'Gracillimus', but this trait was significant in only three of seven tests (Table 5). Inflorescence number appeared to vary greatly from plant to plant (probably environmental effects). Leaf length and width were similar for 'M77' and 'Gracillimus' (Table 6). However, leaves of 'Gracillimus' were significantly longer than those of 'M77' at Tifton in 2013. The data shows (Table 7) that seed set was greatly reduced for 'M77' compared to 'Gracillimus' and statistically significant for all years tested.

Although 'M77' sets a small amount of seed, we wanted to know how many of the seed produced actually germinated. In 2015, we tested the germination of 2014 harvested seed from 'M77' plants from both Tifton, Ga. and Blairsville, Ga. Note: a very large number of inflorescences of 'M77' needed to be harvested at Tifton, Ga. and Blairsville, Ga. in order to get enough seed to germinate of this cultivar. None of the seed from the Tifton, Ga. harvest germinated while only 32% of the seed harvested at Blairsville, Ga. germinated (Table 7), further demonstrating high seed sterility. This characteristic reduces the invasive potential of 'M77', which is especially needed at higher elevations. Seeds were stored in small kraft envelops in the threshing shed for six months. Seeds were then planted in steam-sterilized soil and allowed to germinate for 45 days. During the germination period the seeds went through random wet and dry periods. Seedling emergence was rated at three dates during this period. In 2015, we also tested 75 and 12 clones of 'M77' at Tifton, Ga. and Blairsville, Ga., respectively, for morphological uniformity and seed set. All were seed sterile and morphologically uniform.

TABLE 1

Height of inflorescence of two *Miscanthus sinensis* ornamental grasses ('M77' and 'M90' = var. 'Gracillimus') grown at two locations in Georgia.

| | Tifton, GA | | | | Blairsville, GA | | |
|---|---|---|---|---|---|---|---|
| Entry | 2012 | 2012/2013 | 2013/2014 | 2012/2014 | 2012/2013 | 2013 | 2012/2015 |
| Growth Days | 180 | 182 | 197 | 197 | 154 | 116 | 162 |
| 'M77' | 122 | 111 | 133 | 203 | 200 | 122 | 184 |
| 'M90' | 145 | 143 | 136 | 208 | 212 | 144 | 210 |
| LSD | 11 | 10 | NS | NS | 12 | 11 | NS |

In Table 1, plant height measured from ground level to top of inflorescence. All heights measured are in cm. At Tifton, Ga., 'M77' and 'Gracillimus' were planted 18 Apr. 2012 and 13 Apr. 2013 and measurements were taken 15 Oct. 2012, 30 Sep. 2013, and 9 Sep. 2014, respectively. At Blairsville, Ga., 'M77' and 'Gracillimus' were planted 14 Apr. 2012, and 16 May 2013, and measurements taken 9 Sep. 2013 and 24 Sep. 2015, respectively. Single year is year planted and year data recorded; double years are "year planted/year data recorded".

TABLE 2

Height of leaves of two *Miscanthus sinensis* ornamental grasses ('M77' = experimental and 'M90' = var. 'Gracillimus') grown at two locations in Georgia.

| | Tifton, GA | | | | Blairsville, GA | | |
|---|---|---|---|---|---|---|---|
| Entry | 2012 | 2012/2013 | 2013/2014 | 2012/2014 | 2012/2013 | 2013 | 2012/2015 |
| Growth Days | 180 | 182 | 197 | 197 | 154 | 116 | 162 |
| 'M77' | 66 | 67 | 106 | 136 | 122 | 66 | 151 |
| 'M90' | 90 | 76 | 100 | 140 | 144 | 89 | 140 |
| LSD | 11 | NS | NS | NS | 11 | 10 | NS |

In Table 2, height of leaves were measured from ground level to top of leaf canopy. All height measurements are in cm. At Tifton, Ga., tests were planted 18 Apr. 2012 and 13 Apr. 2013 and measurements were taken 15 Oct. 2012, 30 Sep. 2013, and 9 Sep. 2014. At Blairsville, Ga., tests were planted 14 Apr. 2012, and 16 May 2013, and measurements were taken 9 Sep. 2013 and 24 Sep. 2015. Single year designation is year planted and year data recorded; double years designations are "year planted/year data recorded".

TABLE 3

Canopy diameter of two *Miscanthus sinensis* ornamental grasses ('M77' = experimental and 'M90' = var. 'Gracillimus') grown at two locations in Georgia.

| | Tifton, GA | | | Blairsville, GA | | |
|---|---|---|---|---|---|---|
| | 2012/ 2013 | 2013/ 2014 | 2012/ 2014 | 2013 | 2014 | 2012/ 2015 |
| 'M 77' | 58 | 91 | 151 | 100 | 54 | 184 |
| 'M 90' | 66 | 88 | 153 | 135 | 128 | 159 |
| LSD | NS | NS | NS | 25 | 20 | NS |
| GD | 182 | 197 | 197 | 116 | 130 | 162 |

Canopy diameter measurements are the average diameter of the widest and the narrowest diameter of a single plant canopy. All canopy measurements are in cm. At Tifton, Ga., tests planted were 18 Apr. 2012 and 13 Apr. 2013 and measurements were taken 30 Sep. 2013, and 9 Sep. 2014. At Blairsville, Ga., tests were planted 14 Apr. 2012, and 16 May 2013, and 15 May 2014 and measurements taken 9 Sep. 2013, 22 Sep. 2014 and 24 Sep. 2015. Single year designation is year planted and year data recorded; double years designations are "year planted/year data recorded".

TABLE 4

Inflorescence lengths of two *Miscanthus sinensis* ornamental grasses '(M77' and 'M90' = var. '*Gracillimus*') grown at two locations in Georgia.

| | Tifton | | Blairsville | | |
|---|---|---|---|---|---|
| | 2012 | 2012/2013 | 2013 | 2012/2013 | 2012/2015 |
| Growth Days | 180 | 182 | 116 | 154 | 162 |
| 'M77' | 20 | 36 | 20 | 33 | 28 |
| 'M90' | 26 | 35 | 25 | 32 | 29 |
| LSD | 2 | NS | 2 | NS | NS |

At Tifton, Ga., tests were planted 18 Apr. 2012 and 13 Apr. 2013 and measurements were taken 15 Oct. 2012, and 30 Sep. 2013. At Blairsville, Ga., tests were planted 14 Apr. 2012, and 16 May 2013, and measurements were taken 9 Sep. 2013 and 24 Sep. 2015. All canopy measurements are in cm. Single year designation is year planted and year data recorded; double years designations are "year planted/year data recorded".

TABLE 5

Number of inflorescences of two *Miscanthus sinensis* ornamental grasses ('M77' and 'M90' = var. 'Gracillimus') grown at two locations in Georgia.

| | Tifton, GA | | | | Blairsville, GA | | |
|---|---|---|---|---|---|---|---|
| | 2012 | 2012/ 2013 | 2013/ 2014 | 2012/ 2014 | 2012/ 2013 | 2013 | 2012/ 2015 |
| GD | 180 | 182 | 197 | 197 | 154 | 116 | 162 |
| 'M77' | 23 | 20 | 103 | 86 | 81 | 21 | 133 |
| 'M90' | 34 | 57 | 95 | 127 | 108 | 83 | 153 |
| LSD | 17 | NS | NS | 23 | NS | 37 | NS |

At Tifton, Ga., tests were planted 18 Apr. 2012 and 13 Apr. 2013 and measurements taken 15 Oct. 2012, 30 Sep. 2013, and 9 Sep. 2014. At Blairsville, Ga., tests were planted 14 Apr. 2012, and 16 May 2013, and measurements were taken 9 Sep. 2013 and 24 Sep. 2015. Single year designation is year planted and year data recorded; double years designations are "year planted/year data recorded".

TABLE 6

Leaf length and width of two *Miscanthus sinensis* ornamental grasses ('M77' and 'M90' = var. '*Gracillimus*') grown at two locations in Georgia.

| | Tifton, GA Length 2012/2013 | Blairsville, GA Length 2012/2015 | Tifton, GA Width 2012/2013 | Blairsville, GA Width 2012/2015 |
|---|---|---|---|---|
| Growth Days | 182 | 162 | 182 | 162 |
| 'M 77' | 44 | 68 | 4.37 | 5.2 |
| 'M 90' | 53 | 52 | 4.57 | 5.5 |
| LSD | 6 | NS | NS | NS |

At Tifton, Ga., test was planted 18 Apr. 2012 and measurements were taken 30 Sep. 2013. Leaf length (average from 3 culms) was measured from the leaf collar to the leaf tip of the latest fully extended leaf. At Blairsville, Ga., test was planted 14 Apr. 2012 and measurements were taken 24 Sep. 2015. Leaf width (average from 3 culms) was measured in the center of the latest fully extended leaf. Leaf length measurements are in cm. Leaf width measurements are in mm. Double year designations indicate "year planted/year data recorded".

TABLE 7

Seed set of two *Miscanthus sinensis* ornamental grasses ('M77' and 'M90' = var. 'Gracillimus') grown at two locations in Georgia.

| | Seeds per Inflorescence | | | | | | Seed Germination - % | |
|---|---|---|---|---|---|---|---|---|
| | Tifton, GA | | | Blairsville, GA | | | Tifton | Blairsville |
| Entry | 2012/ 2013 | 2012/ 2014 | 2015 | 2012/ 2013 | 2012/ 2014 | 2012/ 2015 | 2014 | 2014 |
| 'M77' | 0.0 | 7 | 0 | 0.02 | 0.4 | 0 | 0 | 32 |
| 'M90' | 0.02 | 256 | 588 | 24 | 51 | 138 | 42 | 70 |
| LSD | 0.0 | 2 | 129 | 0.0 | 0.0 | 0.0 | 17 | 15 |

At Tifton, Ga., tests were planted 18 Apr. 2012 and 12 May 2015 and seeds were harvested in Oct. of 2013, 2014 and 2015. At Blairsville, Ga., test was planted 14 Apr. 2012, and seeds were harvested in Oct. 2013. 2014 and 2015. Number of seeds per inflorescence was determined from the mean of four random inflorescences from each replication. Seed germination tests was conducted on 25 seeds from four and three different plants (replicatons) harvested in Oct. 2014 at Tifton and Blairsville, Ga. Germination tests were conducted in April of 2015 to allow seeds to go through a dormancy period and simulate field conditions. Double year designations indicate "year planted/year data recorded".

TABLE 8

Summary of morphological characteristics of two *Miscanthus sinensis* cultivars.

| Trait | '*Gracillimus*' | 'M77" |
|---|---|---|
| Mature inflorescence height | 136-210 cm | 111-203 cm |
| Mature leaf height | 76-144 cm | 66-151 cm |
| Diameter of plant canopy | 66-159 cm | 54-184 cm |
| Inflorescence length | 25-35 cm | 20-36 cm |
| Number of Inflorescences per plant | 34-153 | 23-133 |
| Leaf width | 4.6-5.5 mm | 4.4-5.2 mm |
| Leaf length | 52-53 cm | 44-68 cm |
| Adaxial leaf surface trichomes | Glaborous | Glabrous |
| Abaxial leaf surface trichomes | 4-6 mm long | Sparse, less than 0.5 mm long |
| Leaf blade margin trichome length | Abundant, less than 0.5 mm long | Abundant, less than 0.5 mm long |
| Leaf collar trichomes | Dense, 4-6 mm long | Dense, 3-5 mm long |
| Sheath trichomes | Less than 0.5 mm long | Scattered, less than 1 mm long |
| Ligule | Yes. 1-2 mm | Yes, 1-2 mm |
| Ligule trichomes | Dense, 3-4 mm long | Dense, 3-4 mm long |
| Sheath trichomes | Less than 0.5 mm long | Abundant, less than 1 mm long |
| Adaxial leaf color | 143A | 143A |
| Abaxial leaf color | 143A | 143A |
| Midrib color | NN155D | NN155D |

In summary, 'M77' is similar to 'Gracillimus' in height, canopy width, inflorescence length, and leaf characteristics. 'M77' produce significantly fewer seeds than 'Gracillimus' which should greatly reduce the invasiveness of this species.

BRIEF DESCRIPTION OF THE FIGURES

The accompanying colored photographs illustrate the overall appearance and distinct characteristics of the new cultivar of *Miscanthus* 'M77'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart ($5^{th}$ edition, 2007).

Figure 1:
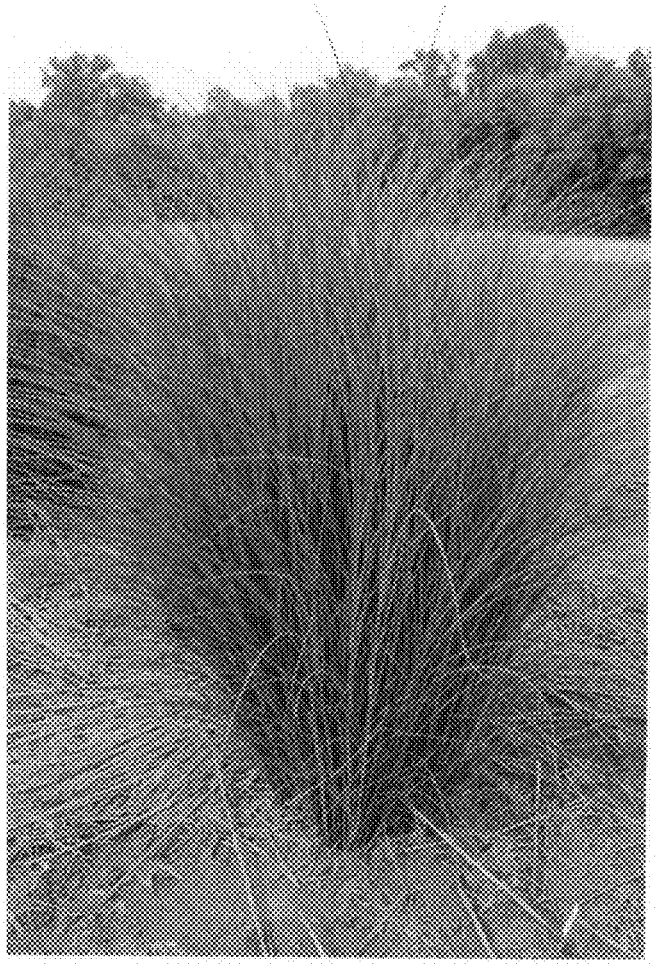
FIG. 1 is a photograph of the vegetative stage of the new cultivar *Miscanthus* 'M77'.
Figure 2:
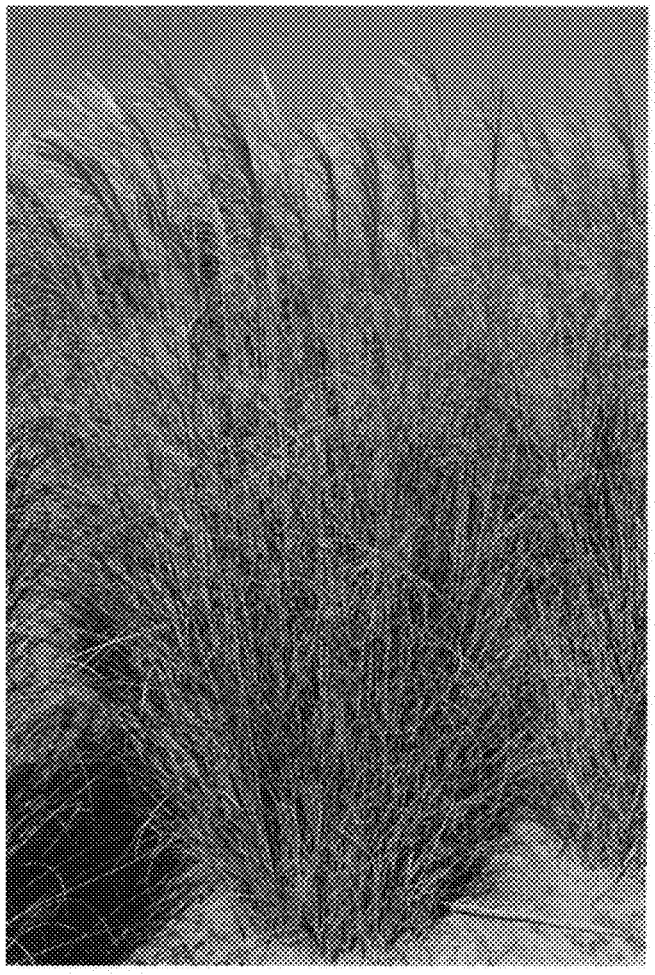
FIG. 2 is a photograph of the flowering stage of the new cultivar *Miscanthus* 'M77'.

The new cultivar 'M77' is a vigorous perennial at Blairsville, Ga. (USDA Zone 7a). The new cultivar 'M77' (i) survived temperatures below 0° C. for 90 days, and a lowest temperature of −9° C., in Blairsville, Ga. during the winter of 2012/2013; (ii) survived temperatures below 0° C. for 95 days, and a lowest temperature of −29° C., in Blairsville, Ga., during the winter of 2013/2014; and (iii) survived temperatures below 0° C. for 101 days, and a lowest temperature of −17° C., in Blairsville, Ga. during the winter of 2014/2015.

All data are from plants established as single stem propagules in mid-April to mid-May and rated in September through October, except the double year dates in the previous tables indicate "year of establishment/year data was collected".

Plant:

*Mature inflorescence height.*—111-203 cm.
*Mature leaf height.*—66-151 cm.
*Diameter of plant canopy.*—54-184 cm.
*Inflorescence length.*—20-36 cm.
*Number of inflorescences per plant.*—23-133.

Leaf:

*Leaf width.*—4.4-5.2 mm.
*Leaf length.*—44-68 cm.
*Adaxial leaf surface trichomes.*—Glabrous.
*Abaxial leaf surface trichomes.*—Sparse, less than 0.5 mm long.
*Leaf blade margin trichome length.*—Abundant, less than 0.5 mm long.
*Leaf collar trichomes.*—Dense, 3-5 mm long.
*Sheath trichomes.*—Scattered, less than 1 mm long.
*Ligule.*—Yes, 1-2 mm.
*Ligule trichomes.*—Dense, 3-4 mm long.
*Sheath trichomes.*—Abundant, less than 1 mm long.
*Adaxial leaf color.*—143A.
*Abaxial leaf color.*—143A.
*Midrib color.*—NN155D.

What is claimed is:

1. A new and distinct cultivar of the *Miscanthus* plant named 'M77', as illustrated and described.

* * * * *